United States Patent [19]
Davila

[11] Patent Number: 5,466,230
[45] Date of Patent: Nov. 14, 1995

[54] CATHETER SHEATH INTRODUCER WITH STRAIN RELIEF

[75] Inventor: Luis A. Davila, Cooper City, Fla.

[73] Assignee: Cordis Corporation, Miami Lakes, Fla.

[21] Appl. No.: 261,087

[22] Filed: Jun. 9, 1994

[51] Int. Cl.[6] ................................... A61M 5/00
[52] U.S. Cl. ................. 604/256; 604/282; 604/283; 138/110
[58] Field of Search ................. 604/282, 283, 604/240, 280, 256; 138/110; 285/114–116

[56] References Cited

U.S. PATENT DOCUMENTS

| | | | |
|---|---|---|---|
| 1,367,246 | 2/1921 | Ewald | 138/110 |
| 1,569,174 | 6/1926 | Crowther | 285/114 |
| 2,185,741 | 1/1940 | Sorg et al. | 285/115 |
| 2,550,669 | 5/1951 | Brickman | 285/115 |
| 3,618,613 | 11/1971 | Shulte | 604/282 |
| 4,430,083 | 2/1984 | Ganz et al. . | |
| 4,610,674 | 9/1986 | Suzuki et al. | 604/282 |
| 4,634,432 | 1/1987 | Kocak . | |
| 4,705,511 | 11/1987 | Kocak . | |
| 4,875,481 | 10/1989 | Higgins . | |
| 5,066,285 | 11/1991 | Hillstead . | |
| 5,143,409 | 9/1992 | Lalikos . | |
| 5,156,594 | 10/1992 | Keith . | |
| 5,167,647 | 12/1992 | Wijkamp et al. . | |
| 5,181,750 | 1/1993 | Reum . | |

*Primary Examiner*—C. Fred Rosenbaum
*Assistant Examiner*—Mark Bockelman
*Attorney, Agent, or Firm*—Gerstman, Ellis & McMillin, Ltd.

[57] ABSTRACT

A catheter sheath introducer comprising a tubular sheath having a proximal end and a distal end are provided. A hub is coupled to the proximal end of the tubular sheath and a coil spring is also provided. The coil spring is positioned about the proximal end of the tubular sheath, and the sheath and coil spring are coupled to the hub in such a way that the tubular sheath and coil spring extend within the hub and out from the hub whereby the strain produced when the tubular sheath and hub are moved relative to one another is relieved.

19 Claims, 3 Drawing Sheets

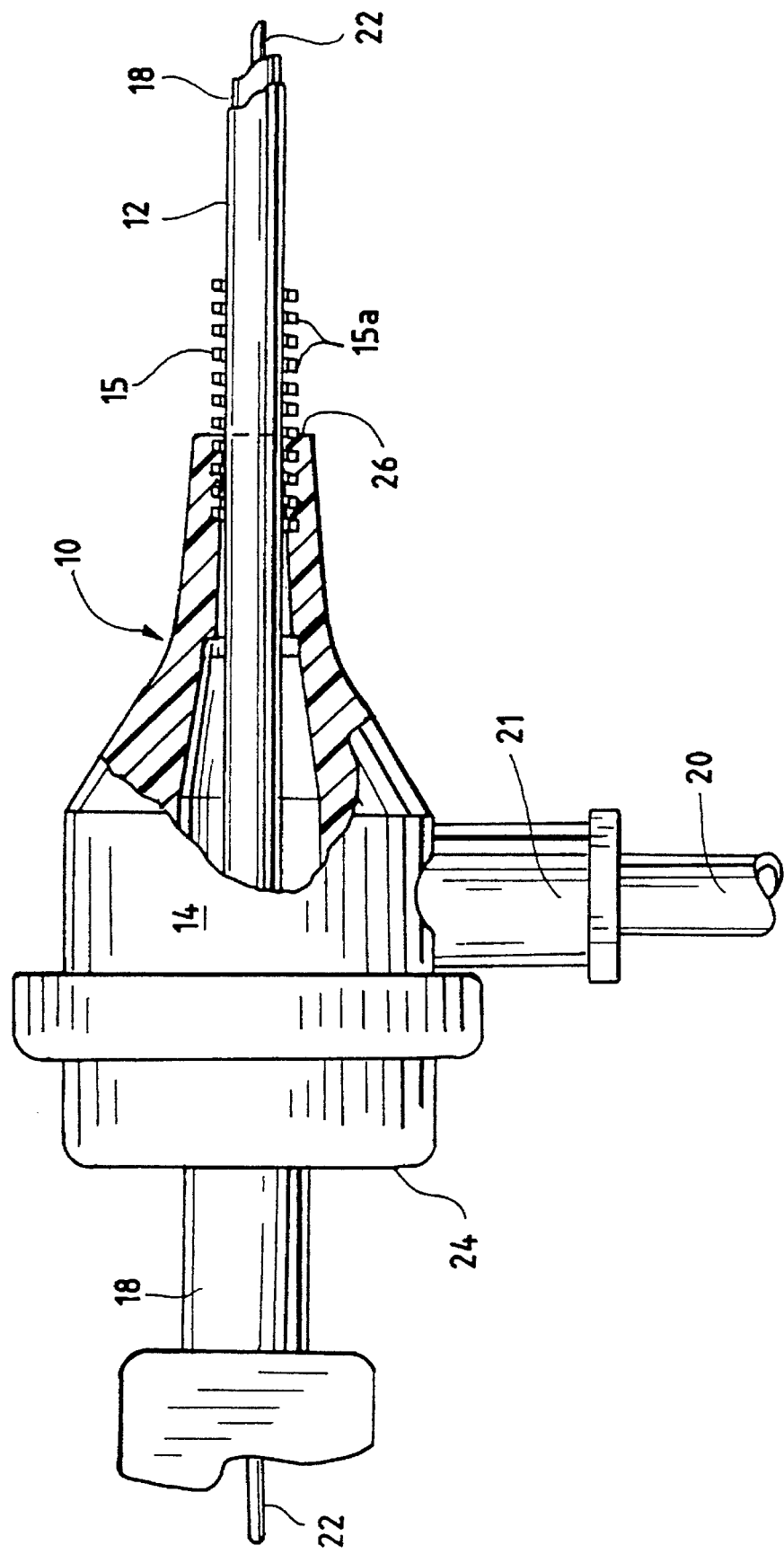

CATHETER SHEATH INTRODUCER WITH STRAIN RELIEF

FIELD OF THE INVENTION

The present invention concerns a novel catheter sheath introducer.

BACKGROUND OF THE INVENTION

Catheter sheath introducers are well known in the health care industry as a means of providing access to the circulatory system for a number of applications. In a now well know process, the catheter sheath introducer is placed in a desired blood vessel to facilitate various procedures. Among these medical procedures is balloon angioplasty which requires the manipulation of long catheters through the circulatory system. Often much manipulation is needed to guide such catheters to the desired position in the body to effect the medical procedure. This manipulation causes strain to develop on the catheter introducer. Further, the mere lifting of the external parts of the introducer while it is in place causes strain between the sheath and the body of the introducer.

Catheter introducers have necessarily small parts with thin walls and small joining surfaces, as for example between the tubular sheath and hub, to allow for insertion into relatively small blood vessels. These small parts are susceptible to kinking and bending under the considerable strain produced when a catheter is introduced and subsequently moved. These movements may result from a medical procedure, the mere manipulation of the emplaced introducer, or simply by the patient rolling over.

Tubular sheaths have been manufactured with rigid plastics to overcome the problems of bending and kinking. Unfortunately, these materials may cause damage to the arterial walls. To avoid such damage to blood vessels, some introducer sheaths have been manufactured with flexible plastic-type materials, having high hoop strengths or with reinforcements, to help stop this kinking and bending while reducing tissue damage. For example, as described in Hillstead U.S. Pat. No. 5,066,285, the tubular sheath of a catheter sheath introducer is made of expanded, fibrous polytetrafluoroethylene (PTFE) so as to produce a more flexible sheath having a high hoop strength that resists kinking. Also, as described in Kocak U.S. Pat. Nos. 4,634, 342 and 4,705,511, the tubular sheath of a catheter sheath introducer is made with a reinforcing helical spring molded into the sheath material so as to provide a flexible tube that is resistant to kinking.

These catheter sheaths are helpful in situations where the entry of the device into the anatomy causes the strain, such as when introducing the sheath through scar tissue. Specialized sheaths of this type are often more difficult to produce and costly to manufacture than regular sheaths. Further, the introduction of the sheath into the anatomy may not be the time at which the greatest strain is placed on all of the different segments of the catheter sheath introducer. Often after the catheter sheath introducer is emplaced the healthcare provider will raise the hub of the introducer so as to insert a catheter. This raising of the hub places a large bending strain on the joining area of the hub and tubular sheath. The tubular sheath may bend or kink in this area as a result of this strain.

It is well known that the joining area of the tubular sheath and the hub is one of the weakest points in a catheter introducer structure. It is also known that this joining area is highly susceptible to strain. Although they are helpful in reducing bending and kinking, the above described sheath tubes may not help to reduce the strain placed at this area of the catheter sheath introducer. Further, although reinforced, a sheath tube such as the device disclosed in the Kocak patents may not have enough reinforcement to prevent the bending caused by the movement of the hub relative to the sheath tube. The results are that the introducers of the prior art are practical for insertion but problems can occur during the subsequent medical procedure.

I have invented a device that utilizes some of the same thin walled sheaths, to allow for comfortable insertion, as the prior introducers and provides a relief for the strain that causes kinking and bending at the joining area between the hub and sheath of the introducer.

It is therefore an object of the present invention to provide a catheter introducer of a size and proportion similar to currently and commercially available catheter introducers with strain relief to prevent kinking and bending of the sheath at the area where the introducer and the tubular sheath meet.

It is a further object of the present invention to provide a catheter sheath introducer with strain relieving means that is easy and economical to construct and use.

Other objects and advantages of the present invention will become apparent as the description proceeds.

SUMMARY OF THE INVENTION

In accordance with the present invention, a catheter sheath introducer comprising a tubular sheath having a proximal end and a distal end are provided. A hub is coupled to the proximal end of the tubular sheath and a coil spring is also provided. The coil spring is positioned about the proximal end of the tubular sheath and the sheath and coil spring are coupled to the hub in such a way that the tubular sheath and coil spring extend within the hub and out from the hub. In this manner, the strain produced when the tubular sheath and hub are moved relative to one another is relieved.

In the illustrative embodiment, the coil spring of the present invention is tightly wound so the space between each coil of the spring is minimized. This provides greater strength against strain in the area of the catheter sheath introducer where the weakest joinder of parts exists while still providing the flexibility necessary to the emplacing of the device.

A more detailed explanation of the invention is provided in the following description and claims and is illustrated in the accompanying drawings.

BRIEF DESCRIPTION OF THE DRAWINGS

FIG. 4 is an enlarged partial elevational view, with portions broken away, of a catheter introducer made in accordance with the present invention, having a coil spring with a rectangular cross-section.

DETAILED DESCRIPTION OF THE ILLUSTRATIVE EMBODIMENT

Figure 1:
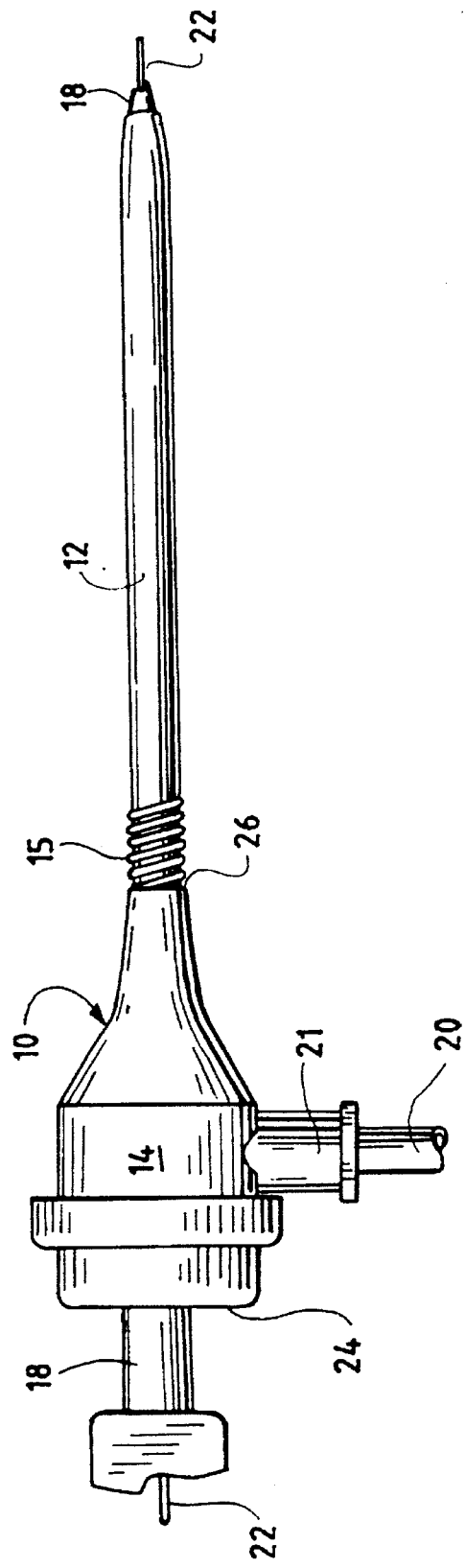
FIG. 1. is an elevational view, partially broken away, of a catheter introducer made in accordance with the present invention.
Figure 2:
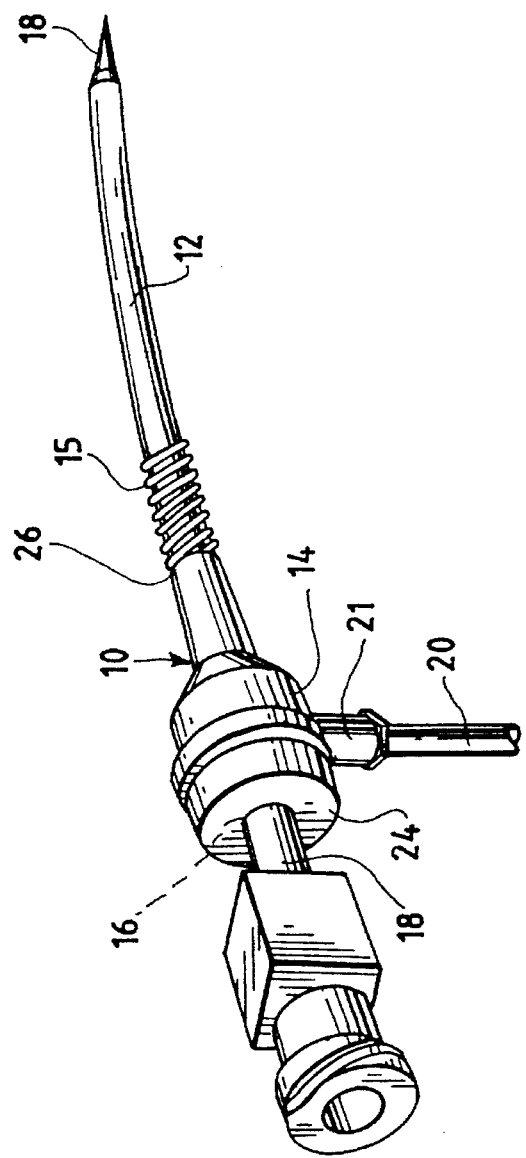
FIG. 2 is a perspective view of a catheter introducer made in accordance with the present invention.

Referring to the drawings, FIGS. 1 and 2 show a catheter sheath introducer 10 having a tubular sheath 12 and a hub 14 attached to the proximal end of sheath 12. A spring 15 is carried on sheath 12 and within hub 14. Catheter sheath introducer 10 is substantially identical to current, commercially available catheter introducers of the prior art except for the modifications of this invention.

Such a catheter sheath introducer usually includes a hemostasis valve 16 to provide sealing of the sheath around a dilator unit 18. A branch conduit 20 and a locking sleeve 21 off of hub 14 is provided to allow for, among other things, connections to saline solution or medicines and access to other medical procedures. An end cap 24 is provided at the proximal end of hub 14. A guide wire 22 is also shown as it is often used with such devices as balloon angioplasty catheters.

Figure 3:
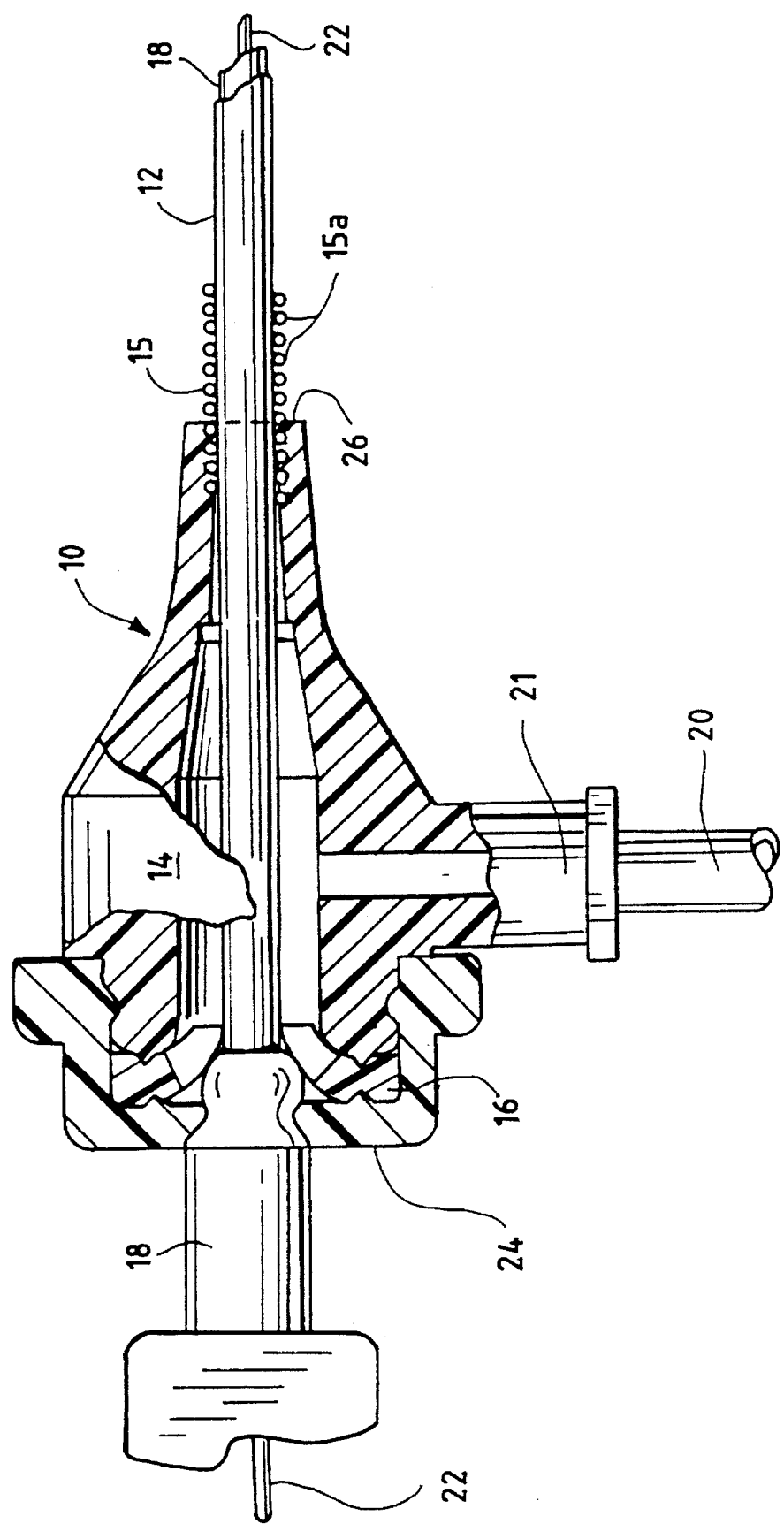
FIG. 3 is an enlarged partial elevational view, with portions broken away, of the catheter introducer of FIG. 1.

FIG. 3 shows catheter sheath introducer 10 cut away to expose some of the internal structure. Sheath 12 is joined to the internal body of hub 14. Spring 15 is wound about sheath 12 and is coupled to hub 14 at its distal end 26. As shown in FIGS. 3 and 4, spring 15 is wound tightly so as to minimize the spacing between coils 15a of spring 15. Spring 15 has a length ranging between 0.500 inch and 0.650 inch, but preferably 0.575 inch. Spring 15 is wound to between 100 and 130 coils, but preferably 115 coils are used. Spring 15 extends within hub 14 on sheath 12 for a specified distance, from the distal end 26 of hub 14, ranging between 0.175 inch and 0.250 inch, but preferably 0.2125 inch. The remainder of the length of spring 15 extends out from the distal end 26 of hub 14, on sheath 12. Spring 15 is made of wire having a gauge of between 0.005 inch and 0.008 inch, preferably 0.0065 inch. The spring can have a rectangular cross-section, as shown in FIG. 4, or round cross-section and can be made of stainless steel or nylon or other biocompatible materials.

The strain caused by the bending action between the sheath 12 and the hub 14 upon insertion and movement of the sheath 12 into the anatomy, is absorbed by spring 15. In this way, movement that would otherwise cause bending or kinking in sheath 12 is absorbed by spring 15. As the spring 15 has a natural ability to absorb strain, sheath 12 does not bend or kink under the ordinary strain produced by the use of catheter sheath introducer 10.

In the process of manufacturing the catheter sheath introducer 10, sheath 12 is placed on a core pin having nearly the same diameter as the inner diameter of sheath 12. Spring 15 is placed near the proximal end of sheath 12 and part of the spring 15 and the proximal end of sheath 12 are placed inside of a mold cavity. A molten plastic-type material is then injected into the mold cavity as approximately 30 tons of pressure are applied to the mold cavity. The injected plastic-type material assumes the shape of the inside of the mold cavity which is the shape of hub 14. When allowed to cool the catheter sheath introducer 10 comprises a hub 14 a sheath 12 and a spring 15 connected together with spring 15 embedded in the plastic of hub 14.

Although an illustrative embodiment of the invention has been shown and described, it is to be understood that various modifications and substitutions may be made by those skilled in the art without departing from the novel spirit and scope of the invention.

What is claimed is:

1. A catheter sheath introducer comprising:

a hub;

a hemostasis valve within said hub;

a tubular sheath having a proximal end and a distal end;

said proximal end of said tubular sheath being molded to said hub;

a coil spring having a smaller length than the length of said tubular sheath;

said coil spring tightly and unattachedly overlying said proximal end of said tubular sheath;

said coil spring being molded to said hub such that said proximal end of said tubular sheath and coil spring extend within said hub and extend out from said distal end of said hub whereby the strain produced when said tubular sheath and hub are moved relative to one another is relieved.

2. The catheter sheath introducer of claim 1, wherein said coil spring is tightly wound whereby the space between the coils of said spring is minimized.

3. The catheter sheath introducer of claim 1, wherein said coil spring has a rectangular cross-section.

4. The catheter sheath introducer of claim 1, wherein said coil spring has a circular cross-section.

5. The catheter sheath introducer of claim 1, wherein said coil spring has a length in the range of 0.500 inch and 0.650 inch.

6. The catheter sheath introducer of claim 1, wherein said coil spring extends from 0.175 inch to 0.250 inch into said hub.

7. The catheter sheath introducer of claim 1, wherein said coil spring is wound to between 100 and 130 coils.

8. The catheter sheath introducer of claim 1, wherein said coil spring is constructed of stainless steel.

9. The catheter sheath introducer of claim 1, wherein said coil spring is constructed of nylon.

10. The catheter sheath introducer of claim 1, wherein said coil spring has a diameter equal to the outer diameter of said tubular sheath.

11. The catheter sheath introducer of claim 1 in which the distal end of said tubular sheath and said coil spring are embedded in said hub.

12. A catheter sheath introducer comprising:

a hub;

a hemostasis valve within said hub;

a tubular sheath having a proximal end and a distal end;

said proximal end of said tubular sheath being molded to said hub;

a coil spring having a smaller length than the length of said tubular sheath;

said coil spring tightly and unattachedly overlying said proximal end of said tubular sheath;

said coil spring being tightly wound so that the space between the coils of said spring is minimized; said coil spring being molded in said hub such that said proximal end of said tubular sheath and coil spring extend within said hub and extend out from said distal end of said hub whereby the strain produced when said tubular sheath and hub are moved relative to one another is relieved.

13. The catheter sheath introducer of claim 12, wherein said coil spring has a rectangular cross-section.

14. The catheter sheath introducer of claim 12, wherein said coil spring has a circular cross-section.

15. The catheter sheath introducer of claim 12, wherein said coil spring is constructed of stainless steel.

16. The catheter sheath introducer of claim 12, wherein said coil spring is constructed of nylon.

17. The catheter sheath introducer of claim 12, wherein said coil spring has a length in the range of 0.500 inch and 0.650 inch.

18. The catheter sheath introducer of claim 12, wherein said coil spring extends from 0.175 inch to 0.250 inch into said hub.

19. The catheter sheath introducer of claim 12, wherein said coil spring is wound to between 100 and 130 coils.

* * * * *